United States Patent [19]
Fullerton

[11] Patent Number: 5,276,265
[45] Date of Patent: Jan. 4, 1994

[54] INBRED CORN LINE PHR31

[75] Inventor: Samuel G. Fullerton, Huron, S. Dak.

[73] Assignee: Pioneer Hi-Bred International, Inc., Des Moines, Iowa

[21] Appl. No.: 831,036

[22] Filed: Feb. 3, 1992

[51] Int. Cl.$^5$ .................. A01H 5/00; A01H 1/00; A01H 4/00; C12N 5/04
[52] U.S. Cl. ................... 800/200; 800/250; 800/DIG. 56; 435/240.4; 435/240.49; 435/240.5; 47/58
[58] Field of Search . 800/200, 205, 250, DIG. 56, 235; 47/58, DIG. 1, 58.03; 435/240.4, 240.45, 240.49

[56] References Cited

PUBLICATIONS

Conger et al. "Somatic Embryogenesis from Cultured Leaf Segments of Zea Mays". Plant Cell Reports 6: 345-347 (1987).
Rao et al. (1986) "Somatic Embryogenesis in Glume Callus Cultures" Maize Genetic Newsletter vol. 60 pp. 64-65.
Songstad et al. (1988) "Effects of ACC, Silver Nitrate & Norbornadiene on Plant Regeneration from Maize Callus Culture", Plant Cell Reports 7:262-265.
Duncan et al. (1985) "The Production of Callus Capable of Plant Regeneration from Immature-Embryos of Numerous Zea Mays Genotypes" Planta 165:332-332.
Meghji et al. (1984) Crop Science vol. 24 pp. 545-549.
Poehlman. (1987) Breeding Field Crops AVI Publishing Co. pp. 237-247.

Primary Examiner—Gary Benzion
Attorney, Agent, or Firm—Nina L. Pearlmutter; Michael J. Roth; Patricia A. Sweeney

[57] ABSTRACT

According to the invention, there is provided an inbred corn line, designated PHR31. This invention thus relates to the plants and seeds of inbred corn line PHR31 and to methods for producing a corn plant produced by crossing the inbred line PHR31 with itself or with another corn plant. This invention further relates to hybrid corn seeds and plants produced by crossing the inbred line PHR31 with another corn line or plant.

10 Claims, No Drawings

INBRED CORN LINE PHR31

FIELD OF THE INVENTION

This invention is in the field of corn breeding, specifically relating to an inbred corn line designated PHR31.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and fruit height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \to F_2$; $F_2 \to F_3$; $F_3 \to F_4$; $F_4 \to F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility of the crop to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

At Pioneer Hi-Bred International, a typical corn research station has a staff of four, and 20 acres of breeding nursery. Those researchers plant those 20 acres with 25,000 nursery rows, 15,000 yield test plots in 10-15 yield test sites, and one or two disease-screening nurseries. Employing a temporary crew of 20 to 30 pollinators, the station makes about 65,000 hand pollinations per growing season, and produces from three to ten new inbreds which are proposed for commercial use each year. Over the 32 Pioneer research stations in North America, this amounts to from about 100 to 300 new inbreds proposed each year from over 2,000,000 pollinations. Of those, less than 50 and more commonly less than 30 are actually selected for commercial use.

SUMMARY OF THE INVENTION

According to the invention, there is provided a novel inbred corn line, designated PHR31. This invention thus relates to the seeds of inbred corn line PHR31, to the plants of inbred corn line PHR31, and to methods for producing a corn plant produced by crossing the inbred line PHR31 with itself or another corn line. This invention further relates to hybrid corn seeds and plants produced by crossing the inbred line PHR31 with another corn line.

DEFINITIONS

In the description and examples that follow, a number of terms are used herein. In order to provide a clear and consistent understanding of the specification and claims, including the scope to be given such terms, the following definitions are provided. ABS is in absolute terms and % MN is percent of the mean for the experiments in which the inbred or hybrid was grown.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest in bushels per acre adjusted to 15.5% moisture.

DRP EAR=DROPPED EARS. A measure of the number of dropped ears per plot and represents the percentage of plants that did not drop ears prior to harvest.

EAR HT=EAR HEIGHT. The ear height is a measure from the ground to the highest placed developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic factors, be produced in a cytoplasmic male-sterile form which is otherwise phenotypically identical to the male-fertile form.

PRM=PREDICTED RM. This trait, predicted relative maturity (RM), is based on the harvest moisture of the grain. The relative maturity rating is based on a known set of checks and utilizes standard linear regression analyses and is referred to as the Comparative Relative Maturity Rating System which is similar to the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV=Maize Dwarf Mosaic Virus & MCDV=Maize Chlorotic Dwarf Virus): Visual rating (1-9 score) where a "1" is very susceptible and a "9" is very resistant.

SLF BLT=Southern Leaf Blight (*Bipolaris maydis, Helminthosporium maydis*): Visual rating (1-9 score) where a "1" is very susceptible and a "9" is very resistant.

NLF BLT=Northern Leaf Blight (*Exserohilum turcicum, H. turcicum*): Visual rating (1-9 score) where a "1" is very susceptible and a "9" is very resistant.

COM RST=Common Rust (*Puccinia sorghi*): Visual rating (1-9 score) where a "1" is very susceptible and a "9" is very resistant.

GLF SPT=Gray Leaf Spot (*Cercospora zeae-maydis*): Visual rating (1-9 score) where a "1" is very susceptible and a "9" is very resistant.

STW WLT=Stewart's Wilt (*Erwinia stewartii*): Visual rating (1-9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1-9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2=SC European Corn Borer Second Brood (*Ostrinia nubilalis*): Visual rating (1-9 score) of post flowering damage due to infestation by European Corn Borer. A "1" is very susceptible and a "9" is very resistant.

ECB 1LF=European Corn Borer First Brood (*Ostrinia nubilalis*): Visual rating (1-9 score) of pre-flowering leaf feeding by European Corn Borer. A "1" is very susceptible and a "9" is very resistant.

DETAILED DESCRIPTION OF THE INVENTION

Inbred corn line PHR31 is a yellow, dent corn inbred that is best suited as a male in crosses for producing first generation F1 corn hybrids. PHR31 is best adapted to the North-Central part of the United States. The inbred can be used to produce hybrids from approximately 101 to 115 relative maturity based on the Minnesota Relative Maturity Rating System for harvest moisture of grain. The inbred has good tolerance to European corn borer and Goss' wilt. In hybrid combination, the inbred has high yield and produces large U ears. In inbred per se and in hybrid combination, kernel abortion at ear tips may occur.

The inbred has shown uniformity and stability within the limits of environmental influence for all the traits as described in the Variety Description Information (Table 1) that follows. Most of the data in the Variety Description information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHR31.

Inbred corn line PHR31, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

VARIETY DESCRIPTION INFORMATION INBRED = PHR31

Type: Dent
Region Best Adapted: Northcentral
A. Maturity: Average across maturity zones. Zone: 0
GDU Shed: 1410
GDU Silk: 1450
No. Reps: 75
B. Plant Characteristics:
Plant height (to tassel tip): 197 cm
Length of top ear internode: 11 cm
Number of ears per stalk: Single
Ear height (to base of top ear): 76 cm
Number of tillers: None
Cytoplasm type: Normal
C. Leaf:
Color: Medium Green (WF9)
Angle from Stalk: <30 degrees
Marginal Waves: Few (WF9)
Number of Leaves (mature plants): 18
Sheath Pubescence: Light (W22)
Longitudinal Creases: Few (OH56A)
Length (Ear node leaf): 76 cm
Width (widest point, ear node leaf): 8 cm
D. Tassel:
Number lateral branches: 11

TABLE 1-continued
VARIETY DESCRIPTION INFORMATION
INBRED = PHR31

Branch Angle from central spike: >45 degrees
Pollen Shed: Heavy based on Pollen Yield Test
(138% of experiment means)
Peduncle Length (top leaf to basal brances): 15 cm
Anther Color: Red
Glume Color: Green
E. Ear (Husked Ear Data Except When Stated Otherwise):
Length: 17 cm
Weight: 121 gm
Mid-point Diameter: 42 mm
Silk Color: Yellow
Husk Extension (Harvest stage): Medium (Barely covering ear)
Husk Leaf: Long (>15 cm)
Taper of Ear: Slight
Position of Shank (dry husks): Upright
Kernel Rows: Straight, Distinct Number = 14
Husk Color (fresh): Light Green
Husk Color (dry): Buff
Shank Length: 13 cm
Shank (No of internodes): 7
F. Kernel (Dried):
Size (from ear mid-point)
Length: 10 mm
Width: 8 mm
Thick: 4 mm
Shape Grade (% rounds): 20-40 (27% medium round based on Parent Test Data)
Pericarp Color: Colorless
Aleurone Color: Homozygous Yellow
Endosperm Color: Yellow
Endosperm Type: Normal Starch
Gm Wt/100 Seeds (unsized): 27 gm
G. Cob:
Diameter at mid-point: 23 mm
Strength: Strong
Color: Red
H. Diseases:
Corn Lethal Necrosis (MCMV = Maize
Chlorotic Mottle Virus and MDMV = Maize
Dwarf Mosaic Virus): Intermediate
Anthracnose Stalk Rot (C. graminicola): Susceptible
N. Leaf Blight (E. turcicum): Susceptible
Common Rust (P. sorghi): Resistant
Gray Leaf Spot (C. zeae): Suscpetible
Stewart's Wilt (E. stewartii): Resistant
Goss's Wilt (C. nebraskense): Resistant
Fusarium Ear Mold (F. moniliforme): Intermediate
I. Insects:
European Corn Borer-1 Leaf Damage (Pre-flowering): Resistant
European Corn Borer-2 (Post-flowering): Susceptible
The above descriptions are based on a scale of 1-9, 1 being hightly susceptible, 9 being highly resistant.
S (Susceptible): Would generally represent a score of 1-3.
I (Intermediate): Would generally represent a score of 4-5.
R (Resistant): Would generally represent a score of 6-7.
H (Highly Resistant): Would generally represent a score of 8-9. Highly resistant does not
imply the inbred is immune.
J. Variety Most Closely Resembling:
Character Inbred
Maturity G50
Usage G50

In interpreting the foregoing color designations, reference may be had to the Munsell Glossy Book of Color, a standard color reference.

G50 (PVP Certificate No. 8300143) is a Pioneer Hi-Bred International, Inc. proprietary inbred.

Data for Items B, C, D, E, F, and G is based primarily on a maximum of eight reps from Johnston, Iowa grown in 1989, 1990 and 1991 plus description information from the maintaining station.

ELECTROPHORESIS RESULTS

Isozyme Genotypes for PHR31

Isozyme data were generated for inbred corn line PHR31 according to the procedures described in Stuber, C. W., Wendel, J. F., Goodman, M. M., and Smith, J. S. C., "Techniques and Scoring Procedures for Starch Gel Electrophoresis of Enzymes from Maize (Zea mays L.)", Technical Bulletin No. 286, North Carolina Agricultural Research Service, North Carolina State University, Raleigh, N.C. (1988).

The data in Table 2 compares PHR31 with its parents, G50 and PHRH7.

TABLE 2
ELECTROPHORESIS RESULTS FOR PHR31 AND ITS PARENTS G50 AND PHRH7

| LOCI | PHR31 | PARENTS | |
|------|-------|---------|---|
|      |       | G50     | PHRH7 |
| ACP1 | 2 | 4 | 2 |
| ADH1 | 4 | 4 | 4 |
| CAT3 | 9 | 9 | 9 |
| DIA1 | 8 | 8 | 8 |
| GOT1 | 4 | 4 | 4 |
| GOT2 | 4 | 4 | 2 |
| GOT3 | 4 | 4 | 4 |
| IDH1 | 4 | 4 | 4 |
| IDH2 | 6 | 6 | 4 |
| MDH1 | 1 | 6 | 6 |
| MDH2 | 3.5 | 3.5 | 3.5 |
| MDH3 | 16 | 16 | 16 |
| MDH4 | 12 | 12 | 12 |
| MDH5 | 12 | 12 | 12 |
| MMM  | 4 | 4 | 4 |
| PGM1 | 9 | 9 | 9 |
| PGM2 | 4 | 4 | 4 |
| PGD1 | 3.8 | 3.8 | 2 |
| PGD2 | 5 | 5 | 5 |
| PHI1 | 4 | 4 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHR31. Further, both first and second parent corn plants can come from the inbred corn line PHR31. Thus, any such methods using the inbred corn line PHR31 are part of this invention: selfing, backcrosses, hybrid production, crosses to populations, and the like. All plants produced using inbred corn line PHR31 as a parent are within the scope of this invention. Advantageously, the inbred corn line is used in crosses with other, different, corn inbreds to produce first generation ($F_1$) corn hybrid seeds and plants with superior characteristics.

As used herein, the term plant includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Duncan, Williams, Zehr, and Widholm, *Planta*, (1985) 165:322-332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in Plant Cell Reports (1988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous *Zea Mays* Genotypes," 165 *Planta* 322–332 (1985). Thus, another aspect of this invention is to provide cells which upon growth and differentiation produce corn plants having the physiological and morphological characteristics of the inbred line PHR31.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHR31, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE 3

Inbred and Hybrid Performance of PHR31

In the examples that follow, the traits and characteristics of inbred corn line PHR31 are given as a line and in hybrid combination. The data collected on inbred corn line PHR31 is presented for the key characteristics and traits.

The results in Table 3A compare PHR31 to its G50 parent. The results show PHR31 has higher yield and grain harvest moisture, but lower test weight than G50. The PHR31 inbred has a bigger ear than the G50 parent. PHR31 is taller with lower ear placement and flowers (GDU Shed and GDU Silk) earlier than G50. PHR31 and G50 have similar pollen weight, but PHR31 has a smaller tassel. PHR31 has fewer scattergrain and has better stay green than G50. PHR31 is more susceptible to stalk and root lodging than G50. PHR31 has better common rust resistance, but is more susceptible to Northern leaf blight and first and second brood European corn borer than G50.

Table 3B compares PHR31 to its other parent, PHRH7. PHR31 has higher yield, grain harvest moisture, and test weight compared to PHRH7. PHR31 and PHRH7 have similar plant height, but PHR31 has lower ear placement. PHR31 flowers (GDU Shed and GDU Silk) later than PHRH7.

Tables 3C through 3E compare PHR31 with other Pioneer Proprietary inbreds with similar genetic backgrounds, similar usage and proven performance in the area where PHR31 is adapted.

The results in Table 3C show PHR31 has lower yield, higher grain harvest moisture, and similar test weight compared to PHJ90. PHR31 is a taller inbred with higher ear placement and flowers (GDU Shed and GDU Silk) later than PHJ90. PHR31 has a greater pollen weight and larger tassel than PHJ90. PHR31 has poorer grain appearance, more scattergrain, and better stay green than PHJ90. PHR31 and PHJ90 have similar stalk lodging resistance, but PHR31 is more susceptible to root lodging. PHR31 has better resistance to common rust, gray leaf spot, head smut, and second brood European corn borer, but is more susceptible to ear mold and Northern leaf blight than PHJ90.

Table 3D compares PHR31 to PHP02. The results show PHR31 has higher yield, grain harvest moisture, and similar test weight compared to PHP02. PHR31 has larger ears than PHP02. PHR31 is a taller inbred with higher ear placement and flowers (GDU Shed and GDU Silk) later than PHP02. PHR31 has a greater pollen weight and a larger tassel than PHP02. PHR31 has better stay green and is more susceptible to stalk and root lodging than PHP02. PHR31 has better resistance to common rust, Stewart's wilt, and first and second brood European corn borer, but is more susceptible to Northern leaf blight than PHP02.

The results in Table 3E show PHR31 has higher yield and grain harvest moisture, and similar test weight compared to PHG29. PHR31 has a larger ear and fewer barren plants than PHG29. PHR31 is taller with higher ear placement and flowers (GDU Shed and GDU Silk) later than PHG29. PHR31 and PHG29 have similar tassel size, but PHR31 has a greater pollen weight. PHR31 has more scattergrain and better stay green than PHG29. PHR31 and PHG29 have similar stalk lodging resistance, but PHR31 is more susceptible to root lodging. PHR31 has better resistance to first and second brood European corn borer, but is more susceptible to ear mold, head smut, and Northern leaf blight than PHG29.

The results in Table 4A compare PHR31 to PHJ90 crossed to the same inbred testers. The results show the PHR31 and PHJ90 hybrids have similar yield and grain harvest moisture, but the PHR31 hybrids have slightly higher test weight. The PHR31 and PHJ90 hybrids have similar stalk lodging resistance, but the PHR31 hybrids are more susceptible to root lodging. The PHR31 hybrids have better stay green and poorer seedling vigor compared to the PHJ90 hybrids. The PHR31 hybrids are taller with higher placement and have fewer brittle stalks than the PHJ90 hybrids.

Table 4B compares PHR31 to PHP02 crossed to the same inbred testers. PHR31 hybrids have higher yield and test weight, and slightly lower grain harvest moisture than PHP02 hybrids. PHR31 hybrids have slightly better stay green, better grain appearance, and better seedling vigor than PHP02 hybrids. The PHR31 hybrids are taller with higher ear placement than the PHP02 hybrids.

The results in Table 4C compare PHR31 to PHPT1 crossed to the same inbred testers. In this comparison, PHR31 hybrids have higher yield, grain harvest moisture, and test weight than PHPT1 hybrids. PHR31 hybrids shed (GDU Shed) later than PHPT1 hybrids. The PHR31 hybrids have better stalk lodging resistance but are more susceptible to root lodging than the PHPT1 hybrids. PHR31 hybrids have better grain appearance, but have poorer seedling vigor and a lower early stand count compared to PHPT1 hybrids. The PHR31 hybrids are taller with higher ear placement and have fewer brittle stalks than the PHPT1 hybrids.

TABLE 3A

PAIRED INBRED COMPARISON DATA
VARIETY #1 - PHR31
VARIETY #2 - G50

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | TIL LER ABS | GDU SHD ABS | GDU SLK ABS | POL WT ABS |
|---|---|---|---|---|---|---|---|---|---|---|---|---|---|---|---|
| TOTAL SUM | 1 | 84.9 | 152 | 6.5 | 22.8 | 7.0 | 97.7 | 71.8 | 28.1 | 5.1 | 32.0 | 2.4 | 1396 | 1427 | 193.0 |
|  | 2 | 56.7 | 98 | 5.1 | 19.2 | 5.4 | 96.2 | 69.3 | 29.0 | 3.7 | 27.3 | 2.0 | 1408 | 1432 | 192.7 |
|  | LOCS | 3 | 3 | 17 | 3 | 11 | 17 | 24 | 24 | 34 | 68 | 38 | 67 | 66 | 8 |
|  | REPS | 6 | 6 | 19 | 6 | 11 | 20 | 35 | 38 | 133 | 50 | 87 | 86 | 16 |  |
|  | DIFF | 28.2 | 54 | 1.4 | 3.6 | 1.6 | 1.5 | 2.4 | 1.0 | 1.4 | 4.7 | 0.5 | 12 | 05 | 0.2 |
|  | PROB | .022+ | .092* | .007# | .180 | .001# | .271 | .066* | .352 | .000# | .000# | .558 | .016+ | .312 | .993 |

| DEPT | VAR # | POL WT % MN | POL SC ABS | TAS BLS ABS | TAS SZ ABS | TEX EAR ABS | TST WT ABS | SCT GRN ABS | STA GRN ABS | STK LDG ABS |
|---|---|---|---|---|---|---|---|---|---|---|
| TOTAL SUM | 1 | 139 | 6.6 | 9.0 | 7.1 | 5.2 | 55.5 | 6.7 | 5.4 | 91.4 |
|  | 2 | 138 | 6.7 | 9.0 | 7.6 | 7.2 | 57.8 | 5.7 | 4.4 | 94.3 |
|  | LOCS | 8 | 23 | 3 | 17 | 10 | 3 | 18 | 11 | 2 |
|  | REPS | 16 | 33 | 5 | 19 | 10 | 6 | 20 | 14 | 4 |
|  | DIFF | 1 | 0.0 | 0.0 | 0.5 | 2.0 | 2.4 | 1.0 | 1.0 | 2.9 |
|  | PROB | .947 | .889 | 1.00 | .045+ | .008# | .208 | .023+ | .094* | .664 |

| DEPT | VAR # | RT LDG ABS | COM RST ABS | EAR MLD ABS | GLF SPT ABS | NLF BLT ABS | ECB 1LF ABS | ECB 2SC ABS |
|---|---|---|---|---|---|---|---|---|
| TOTAL SUM | 1 | 42.5 | 7.8 | 5.7 | 1.0 | 2.3 | 7.4 | 4.8 |
|  | 2 | 70.9 | 4.5 | 5.8 | 1.0 | 3.0 | 7.8 | 5.0 |
|  | LOCS | 4 | 4 | 15 | 1 | 10 | 26 | 10 |
|  | REPS | 6 | 4 | 17 | 1 | 11 | 26 | 11 |
|  | DIFF | 28.5 | 3.3 | 0.1 | 0.0 | 0.7 | 0.4 | 0.3 |
|  | PROB | .157 | .032+ | .824 |  | .066* | .039+ | .622 |

* = 10% SIG
+ = 5% SIG
= 1% SIG

TABLE 3B

PAIRED INBRED COMPARISON DATA
VARIETY #1 - PHR31
VARIETY #2 - PHRH7

| DEPT | VAR # | BU ACR ABS | BU ACR % MN | MST ABS | EAR PLT ABS | PLT HT ABS | EAR HT ABS | SDG VGR ABS | EST CNT ABS |
|---|---|---|---|---|---|---|---|---|---|
| TOTAL SUM | 1 | 84.9 | 152 | 22.8 | 98.5 | 74.8 | 30.5 | 4.3 | 46.7 |
|  | 2 | 72.1 | 127 | 20.7 | 98.5 | 74.3 | 32.0 | 5.3 | 49.3 |
|  | LOCS | 3 | 3 | 3 | 3 | 2 | 2 | 3 | 3 |
|  | REPS | 6 | 6 | 6 | 6 | 4 | 4 | 6 | 6 |
|  | DIFF | 12.8 | 25 | 2.1 | 0.0 | 0.5 | 1.5 | 1.0 | 2.7 |
|  | PROB | .051* | .122 | .074* | .978 | .705 | .500 | .225 | .202 |

| DEPT | VAR # | TIL LER ABS | GDU SHD ABS | GDU SLK ABS | TST WT ABS | STA GRN ABS | STK LDG ABS | RT LDG ABS | ECB 2SC ABS |
|---|---|---|---|---|---|---|---|---|---|
| TOTAL SUM | 1 | 0.8 | 1460 | 1535 | 55.5 | 7.0 | 91.4 | 21.6 | 5.5 |
|  | 2 | 2.2 | 1440 | 1470 | 54.8 | 6.5 | 91.8 | 25.6 | 5.5 |
|  | LOCS | 3 | 1 | 1 | 3 | 3 | 2 | 2 | 1 |
|  | REPS | 6 | 2 | 2 | 6 | 6 | 4 | 4 | 2 |
|  | DIFF | 1.5 | 20 | 65 | 0.7 | 0.5 | 0.4 | 4.0 | 0.0 |

TABLE 3B-continued

PAIRED INBRED COMPARISON DATA
VARIETY #1 - PHR31
VARIETY #2 - PHRH7

| | PROB | .639 | | .355 | .423 | .868 | .500 | |

*= 10% SIG
+= 5% SIG
= 1% SIG

TABLE 3C

PAIRED INBRED COMPARISON DATA
VARIETY #1 - PHR31
VARIETY #2 - PHJ90

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|---|
| TOTAL SUM | 1 | 87.2 | 125 | 6.7 | 21.1 | 7.0 | 96.8 | 72.4 | 30.9 | 5.3 | 37.2 | 98.8 | 2.0 | 1399 | 1434 |
| | 2 | 90.9 | 131 | 7.0 | 19.2 | 6.9 | 97.9 | 66.6 | 27.8 | 5.5 | 38.3 | 99.5 | 1.3 | 1354 | 1395 |
| | LOCS | 24 | 24 | 23 | 27 | 12 | 33 | 40 | 40 | 43 | 94 | 20 | 48 | 91 | 83 |
| | REPS | 50 | 50 | 25 | 53 | 12 | 39 | 63 | 63 | 55 | 176 | 42 | 65 | 120 | 105 |
| | DIFF | 3.7 | 5 | 0.3 | 2.0 | 0.1 | 1.0 | 5.8 | 3.1 | 0.2 | 1.0 | 0.7 | 0.7 | 46 | 39 |
| | PROB | .217 | .235 | .295 | .000# | .830 | .296 | .000# | .000# | .365 | .007# | .078* | .377 | .000# | .000# |

| DEPT | VAR # | POL WT ABS | POL WT % MN | POL SC ABS | TAS BLS ABS | TAS SZ ABS | TEX EAR ABS | TST WT ABS | GRN APP ABS | SCT GRN ABS | STA GRN ABS | STK LDG ABS | RT LDG ABS | BRT STK ABS | COM RST ABS |
|---|---|---|---|---|---|---|---|---|---|---|---|---|---|---|---|
| TOTAL SUM | 1 | 170.1 | 124 | 6.5 | 9.0 | 7.1 | 4.7 | 55.7 | 5.8 | 6.8 | 4.7 | 84.1 | 79.3 | 99.2 | 7.6 |
| | 2 | 135.4 | 97 | 6.1 | 9.0 | 6.3 | 5.5 | 55.5 | 6.5 | 7.9 | 3.1 | 85.3 | 85.6 | 99.0 | 6.2 |
| | LOCS | 6 | 6 | 27 | 3 | 26 | 11 | 24 | 18 | 19 | 22 | 24 | 13 | 5 | 5 |
| | REPS | 12 | 12 | 35 | 4 | 28 | 11 | 50 | 38 | 21 | 31 | 50 | 24 | 9 | 5 |
| | DIFF | 34.7 | 27 | 0.4 | 0.0 | 0.8 | 0.8 | 0.3 | 0.7 | 1.2 | 1.5 | 1.2 | 6.3 | 0.2 | 1.4 |
| | PROB | .286 | .257 | .143 | 1.00 | .001# | .158 | .265 | .055* | .001# | .000# | .686 | .329 | .810 | .005# |

| DEPT | VAR # | EAR MLD ABS | GLF SPT ABS | GOS WLT ABS | HD SMT ABS | NLF BLT ABS | STW WLT ABS | ECB DPE ABS | ECB 1LF ABS | ECB 2SC ABS | ECB 2IT ABS |
|---|---|---|---|---|---|---|---|---|---|---|---|
| TOTAL SUM | 1 | 5.8 | 2.5 | 8.5 | 79.6 | 2.2 | 6.0 | 93.3 | 7.3 | 4.2 | 20.5 |
| | 2 | 6.8 | 1.2 | 9.0 | 61.6 | 3.5 | 5.5 | 73.3 | 7.1 | 3.0 | 36.6 |
| | LOCS | 17 | 5 | 1 | 4 | 17 | 2 | 1 | 32 | 22 | 1 |
| | REPS | 19 | 8 | 2 | 8 | 24 | 2 | 3 | 37 | 36 | 3 |
| | DIFF | 1.0 | 1.3 | 0.5 | 18.0 | 1.3 | 0.5 | 20.0 | 0.2 | 1.2 | 16.1 |
| | PROB | .044# | .049+ | | .140 | .000# | .500 | | .362 | .000# | |

*= 10% SIG
+= 5% SIG
= 1% SIG

TABLE 3D

PAIRED INBRED COMPARISON DATA
VARIETY #1 - PHR31
VARIETY #2 - PHP02

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS |
|---|---|---|---|---|---|---|---|---|---|---|---|---|---|---|
| TOTAL SUM | 1 | 89.6 | 130 | 6.6 | 23.6 | 6.9 | 97.3 | 73.2 | 30.0 | 5.2 | 38.4 | 99.4 | 2.0 | 1399 |
| | 2 | 79.7 | 115 | 6.3 | 19.0 | 6.1 | 98.2 | 68.5 | 24.4 | 5.1 | 37.9 | 98.8 | 2.1 | 1309 |
| | LOCS | 27 | 27 | 21 | 30 | 13 | 37 | 46 | 46 | 48 | 97 | 19 | 51 | 91 |
| | REPS | 62 | 62 | 23 | 65 | 13 | 52 | 78 | 77 | 63 | 187 | 40 | 77 | 121 |
| | DIFF | 9.8 | 16 | 0.3 | 4.6 | 0.8 | 0.9 | 4.8 | 5.6 | 0.2 | 0.5 | 0.6 | 0.1 | 90 |
| | PROB | .002# | .005# | .353 | .000# | .085* | .313 | .000# | .000# | .419 | .194 | .175 | .938 | .000# |

| DEPT | VAR # | GDU SLK ABS | POL WT ABS | POL WT % MN | POL SC ABS | TAS BLS ABS | TAS SZ ABS | TEX EAR ABS | TST WT ABS | GRN APP ABS | SCT GRN ABS | STA GRN ABS | STK LDG ABS |
|---|---|---|---|---|---|---|---|---|---|---|---|---|---|
| TOTAL SUM | 1 | 1430 | 170.1 | 124 | 6.6 | 9.0 | 7.0 | 5.0 | 54.6 | 5.5 | 6.8 | 5.3 | 91.4 |
| | 2 | 1337 | 136.1 | 96 | 5.9 | 9.0 | 5.6 | 4.1 | 54.6 | 5.8 | 7.0 | 3.8 | 95.9 |
| | LOCS | 84 | 6 | 6 | 25 | 3 | 23 | 11 | 27 | 16 | 19 | 25 | 22 |
| | REPS | 109 | 12 | 12 | 33 | 4 | 25 | 11 | 62 | 34 | 21 | 42 | 47 |
| | DIFF | 92 | 34.0 | 27 | 0.7 | 0.0 | 1.5 | 0.9 | 0.0 | 0.3 | 0.2 | 1.5 | 4.5 |
| | PROB | .000# | .324 | .279 | .010+ | 1.00 | .000# | .064* | .911 | .593 | .611 | .000# | .004# |

| DEPT | VAR # | RT LDG ABS | BRT STK ABS | COM RST ABS | EAR MLD ABS | GLF SPT ABS | NLF BLT ABS | STW WLT ABS | ECB 1LF ABS | ECB 2SC ABS |
|---|---|---|---|---|---|---|---|---|---|---|
| TOTAL SUM | 1 | 75.5 | 99.1 | 7.6 | 5.7 | 1.0 | 2.3 | 6.0 | 7.1 | 4.5 |
| | 2 | 79.4 | 99.7 | 6.0 | 5.9 | 1.0 | 3.7 | 3.5 | 5.4 | 3.8 |
| | LOCS | 12 | 3 | 5 | 16 | 1 | 10 | 2 | 31 | 18 |
| | REPS | 26 | 5 | 5 | 18 | 1 | 11 | 2 | 32 | 28 |
| | DIFF | 3.8 | 0.6 | 1.6 | 0.2 | 0.0 | 1.4 | 2.5 | 1.7 | 0.7 |

TABLE 3D-continued

PAIRED INBRED COMPARISON DATA
VARIETY #1 - PHR31
VARIETY #2 - PHP02

| | | | | | | | | | |
|---|---|---|---|---|---|---|---|---|---|
| PROB | .552 | .657 | .056* | .530 | | .023+ | .126 | .000# | .014+ |

\* = 10% SIG
+ = 5% SIG
= 1% SIG

TABLE 3E

PAIRED INBRED COMPARISON DATA
VARIETY #1 - PHR31
VARIETY #2 - PHG29

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS |
|---|---|---|---|---|---|---|---|---|---|---|---|---|---|---|---|
| TOTAL SUM | 1 | 81.0 | 127 | 6.2 | 18.5 | 6.5 | 97.3 | 73.3 | 30.2 | 5.3 | 33.2 | 98.4 | 2.9 | 1404 | 1433 |
| | 2 | 63.7 | 100 | 6.1 | 17.0 | 5.8 | 95.6 | 68.1 | 25.1 | 4.1 | 32.2 | 99.1 | 2.7 | 1359 | 1399 |
| | LOCS | 17 | 17 | 9 | 20 | 6 | 27 | 27 | 27 | 35 | 61 | 12 | 28 | 58 | 55 |
| | REPS | 34 | 34 | 11 | 37 | 6 | 34 | 44 | 44 | 48 | 132 | 24 | 40 | 81 | 76 |
| | DIFF | 17.3 | 27 | 0.1 | 1.5 | 0.7 | 1.7 | 5.2 | 5.0 | 1.2 | 1.0 | 0.8 | 0.1 | 44 | 34 |
| | PROB | .000# | .000# | .945 | .004# | .444 | .514 | .001# | .000# | .000# | .169 | .327 | .816 | .000# | .000# |

| DEPT | VAR # | POL WT ABS | POL WT % MN | POL SC ABS | TAS SZ ABS | TEX EAR ABS | TST WT ABS | GRN APP ABS | SCT GRN ABS | STA GRN ABS | STK LDG ABS |
|---|---|---|---|---|---|---|---|---|---|---|---|
| TOTAL SUM | 1 | 188.2 | 125 | 6.1 | 6.9 | 5.0 | 56.5 | 6.4 | 6.9 | 4.7 | 82.1 |
| | 2 | 165.3 | 106 | 7.0 | 6.6 | 3.8 | 56.7 | 6.4 | 8.1 | 3.0 | 81.1 |
| | LOCS | 3 | 3 | 11 | 15 | 5 | 17 | 10 | 10 | 14 | 17 |
| | REPS | 6 | 6 | 16 | 17 | 5 | 34 | 20 | 12 | 20 | 34 |
| | DIFF | 22.9 | 19 | 0.9 | 0.3 | 1.2 | 0.2 | 0.0 | 1.2 | 1.7 | 1.0 |
| | PROB | .646 | .600 | .005# | .326 | .374 | .559 | .000 | .009# | .001# | .837 |

| DEPT | VAR # | RT LDG ABS | BRT STK ABS | COM CLN ABS | COM RST ABS | EAR MLD ABS | GLF SPT ABS | GOS WLT ABS | HD SMT ABS | NLF BLT ABS | ECB DPE ABS | ECB 1LF ABS | ECB 2SC ABS | ECB 2IT ABS |
|---|---|---|---|---|---|---|---|---|---|---|---|---|---|---|
| TOTAL SUM | 1 | 68.9 | 99.6 | 5.5 | 7.7 | 5.8 | 2.9 | 8.5 | 79.6 | 2.2 | 84.2 | 7.4 | 4.4 | 20.5 |
| | 2 | 88.6 | 99.6 | 3.0 | 7.0 | 6.5 | 1.6 | 8.0 | 98.3 | 4.5 | 72.5 | 5.0 | 3.0 | 40.5 |
| | LOCS | 11 | 3 | 1 | 3 | 12 | 4 | 1 | 4 | 13 | 2 | 26 | 20 | 1 |
| | REPS | 19 | 5 | 2 | 3 | 14 | 7 | 2 | 8 | 20 | 6 | 36 | 36 | 3 |
| | DIFF | 19.7 | 0.0 | 2.5 | 0.7 | 0.6 | 1.3 | 0.5 | 18.7 | 2.3 | 11.7 | 2.4 | 1.4 | 20.1 |
| | PROB | .016+ | .423 | | .184 | .376 | .141 | | .002# | .000# | .500 | .000# | .000# | .000# |

\* = 10% SIG
+ = 5% SIG
= 1% SIG

TABLE 4A

AVERAGE INBRED BY TESTER PERFORMANCE COMPARING PHR31 TO PHJ90
CROSSED TO THE SAME INBRED TESTERS AND GROWN IN THE SAME EXPERIMENTS.
ALL VALUES ARE EXPRESSED AS PERCENT OF THE EXPERIMENT MEAN EXCEPT
PREDICTED RM, SELECTION INDEX, AND YIELD (BU/ACR).

| | INBRED | PRM | SEL IND | BU ACR | YLD | MST | GDU SHD | PRM SHD | STK LDG | RT LDG | STA GRN |
|---|---|---|---|---|---|---|---|---|---|---|---|
| TOTAL | REPLIC. | 585 | 603 | 622 | 622 | 623 | 187 | 46 | 594 | 289 | 282 |
| MEAN WTS | PHR31 | 106 | 103 | 155 | 102 | 100 | 100 | 105 | 100 | 98 | 95 |
| MEAN WTS | PHJ90 | 106 | 104 | 155 | 103 | 100 | 98 | 104 | 100 | 102 | 93 |
| | DIFF. | | 1 | | 1 | 0 | 1 | 1 | 0 | 3 | 1 |

| | INBRED | TST WTA | GRN APP | SDG VGR | EST CNT | STK CNT | PLT HT | EAR HT | DRP EAR | BRT STK |
|---|---|---|---|---|---|---|---|---|---|---|
| TOTAL | REPLIC. | 621 | 261 | 213 | 278 | 660 | 320 | 320 | 497 | 33 |
| MEAN WTS | PHR31 | 100 | 100 | 95 | 99 | 100 | 100 | 103 | 100 | 98 |
| MEAN WTS | PHJ90 | 99 | 101 | 102 | 99 | 100 | 96 | 97 | 100 | 96 |
| | DIFF. | 1 | 1 | 7 | 0 | 1 | 4 | 5 | 0 | 2 |

TABLE 4B

AVERAGE INBRED BY TESTER PERFORMANCE COMPARING PHR31 TO PHP02
CROSSED TO THE SAME INBRED TESTERS AND GROWN IN THE SAME EXPERIMENTS.
ALL VALUES ARE EXPRESSED AS PERCENT OF THE EXPERIMENT MEAN EXCEPT
PREDICTED RM, SELECTION INDEX, AND YIELD (BU/ACR).

| | INBRED | PRM | SEL IND | BU ACR | YLD | MST | GDU SHD | PRM SHD | STK LDG | RT LDG | STA GRN |
|---|---|---|---|---|---|---|---|---|---|---|---|
| TOTAL | REPLIC. | 236 | 217 | 236 | 236 | 236 | 59 | 22 | 228 | 91 | 123 |
| MEAN WTS | PHR31 | 107 | 104 | 145 | 104 | 102 | 99 | 106 | 101 | 95 | 106 |
| MEAN WTS | PHP02 | 108 | 97 | 139 | 99 | 103 | 97 | 104 | 101 | 96 | 105 |

TABLE 4B-continued

AVERAGE INBRED BY TESTER PERFORMANCE COMPARING PHR31 TO PHP02
CROSSED TO THE SAME INBRED TESTERS AND GROWN IN THE SAME EXPERIMENTS.
ALL VALUES ARE EXPRESSED AS PERCENT OF THE EXPERIMENT MEAN EXCEPT
PREDICTED RM, SELECTION INDEX, AND YIELD (BU/ACR).

|  |  | DIFF. | 1 | 6 | 7 | 4 | 1 | 2 | 3 | 0 | 1 | 1 |
|---|---|---|---|---|---|---|---|---|---|---|---|---|
|  | INBRED | TST WTA | GRN APP | SDG VGR | EST CNT | STK CNT | PLT HT | EAR HT | DRP EAR | BRT STK |
| TOTAL | REPLIC. | 234 | 105 | 80 | 130 | 249 | 113 | 113 | 190 | 11 |
| MEAN WTS | PHR31 | 101 | 103 | 106 | 99 | 100 | 99 | 102 | 100 | 96 |
| MEAN WTS | PHP02 | 99 | 93 | 87 | 99 | 100 | 97 | 95 | 100 | 97 |
|  | DIFF. | 2 | 10 | 19 | 0 | 0 | 2 | 6 | 0 | 1 |

TABLE 4C

AVERAGE INBRED BY TESTER PERFORMANCE COMPARING PHR31 TO PHPT1
CROSSED TO THE SAME INBRED TESTERS AND GROWN IN THE SAME EXPERIMENTS.
ALL VALUES ARE EXPRESSED AS PERCENT OF THE EXPERIMENT MEAN EXCEPT
PREDICTED RM, SELECTION INDEX, AND YIELD (BU/ACR).

|  | INBRED | PRM | SEL IND | BU ACR | YLD | MST | GDU SHD | PRM SHD | STK LDG | RT LDG | STA GRN |
|---|---|---|---|---|---|---|---|---|---|---|---|
| TOTAL | REPLIC. | 54 | 53 | 54 | 54 | 54 | 16 | 8 | 53 | 24 | 13 |
| MEAN WTS | PHR31 | 100 | 106 | 147 | 104 | 98 | 102 | 101 | 99 | 99 | 60 |
| MEAN WTS | PHPT1 | 96 | 96 | 134 | 94 | 90 | 96 | 96 | 97 | 101 | 54 |
|  | DIFF. | 4 | 9 | 13 | 10 | 8 | 6 | 5 | 2 | 2 | 6 |

|  | INBRED | TST WTA | GRN APP | SDG VGR | EST CNT | STK CNT | PLT HT | EAR HT | DRP EAR | BRT STK |
|---|---|---|---|---|---|---|---|---|---|---|
| TOTAL | REPLIC. | 54 | 28 | 7 | 29 | 55 | 17 | 17 | 48 | 4 |
| MEAN WTS | PHR31 | 101 | 110 | 91 | 98 | 100 | 103 | 100 | 100 | 108 |
| MEAN WTS | PHPT1 | 100 | 102 | 105 | 102 | 100 | 98 | 97 | 100 | 95 |
|  | DIFF. | 1 | 8 | 14 | 5 | 0 | 4 | 3 | 0 | 13 |

Applicant has made available to the public without restriction a deposit of at least 2500 seeds of inbred PHR31 with the American Type Culture Collection (ATCC), Rockville, Md. 20852 U.S.A., ATCC Deposit No. 75493, on Jun. 18, 1993. The seeds deposited with the ATCC are taken from the same deposit maintained by Pioneer Hi-Bred International Inc., 700 Capital Square, 400 Locust Street, Des Moines, Iowa 50309 since prior to the filing date of this application. This deposit of the Inbred Corn Line PHR31 will be maintained without restriction in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated PHR31 and having ATCC Accession No. 75493.

2. A corn plant produced by the seed of claim 1.

3. A corn plant having all the physiological and morphological characteristics of the plant of claim 2.

4. A corn plant having the physiological and morphological characteristics of the plant of claim 2, further having cytoplasmic factors conferring male sterility.

5. Tissue culture of regenerable cells of a plant according to claim 2 wherein the tissue regenerates plants having all the morphological and physiological characteristics of PHR31.

6. Tissue culture of a plant according to claim 5, the tissue culture selected from the group consisting of leaves, pollen, embryos, roots, root tips, anthers, silk, flowers, kernels, ears, cobs, husks, stalks and cells and protoplasts thereof.

7. A corn plant regenerated from the tissue culture of claim 5 and having all the physiological and morphological characteristics of PHR31.

8. A method to produce a novel hybrid corn seed comprising the steps of:
(a) planting, in pollinating proximity, seeds of corn inbred lines PHR31 and another inbred line;
(b) cultivating corn plants resulting from said planting until the time the plants bear flowers;
(c) emasculating the flowers of the plants of either inbred line;
(d) allowing natural cross pollinating to occur between said inbred lines; and
(e) harvesting seeds produced on said emasculated plants of the inbred line.

9. An $F_1$ hybrid seed and plant grown therefrom produced by crossing an inbred corn plant according to claim 2 with another, different corn plant according to claim 2 with another, different corn plant and having a genotype one half of which is the genotype of the inbred corn plant of claim 2.

10. Tissue culture of the regenerable cells of the corn plant produced according to claim 9 wherein the culture regenerates a plant having a genotype one half of which is the genotype of PHR31.

* * * * *